United States Patent [19]
Lauhoff et al.

[11] 3,940,996
[45] Mar. 2, 1976

[54] METHOD AND DEVICE FOR REMOTELY MONITORING ELECTRICALLY CONDUCTIVE LIQUIDS

[75] Inventors: Theodor Lauhoff, Bensberg-Herkenrath; Manfred Quante, Bensberg-Immekeppel; Kurt Erwin Stickel, Cologne; Egon Bolz, Heiligenhaus; Klaus Semma, Porzurbach, all of Germany

[73] Assignee: Interatom, Internationale Atomreaktorbau GmbH, Benzberg, Cologne, Germany

[22] Filed: Nov. 19, 1973

[21] Appl. No.: 417,379

Related U.S. Application Data

[63] Continuation of Ser. No. 246,532, April 24, 1972, abandoned.

[30] Foreign Application Priority Data
Apr. 27, 1971   Germany............................ 2120523

[52] U.S. Cl................ 73/432 R; 73/198; 176/19 R
[51] Int. Cl.²......................................... G01R 33/00

[58] Field of Search..... 73/194 EM, 362 R, 362 CP, 73/61 LM, 198, 432 R; 324/30 A, 34 TE, 34 FL, 40; 176/19 R, 19 LD; 336/30

[56] References Cited
UNITED STATES PATENTS

| | | | |
|---|---|---|---|
| 2,267,884 | 12/1941 | Zuschlag............................... | 324/40 |
| 2,435,043 | 1/1948 | Lehde et al..................... | 73/194 EM |
| 2,583,724 | 1/1952 | Broding.......................... | 73/194 EM |
| 2,964,699 | 12/1960 | Perriam et al..................... | 324/40 X |
| 3,164,993 | 1/1965 | Schmidt............................ | 73/362 R |
| 3,197,722 | 7/1965 | Chass.................................. | 336/30 |
| 3,433,057 | 3/1969 | Halsey........................ | 73/194 EM X |
| 3,657,640 | 4/1972 | Jelinek et al.................. | 324/30 A X |

*Primary Examiner*—Charles A. Ruehl
*Attorney, Agent, or Firm*—Herbert L. Lerner

[57] ABSTRACT

An exchangeable measuring head is secured to a flexible or rigid manipulating tube and is slidingly directed in a guide tube to a measuring location. The measuring head contains three induction coils for measuring bubble content, for instantaneously detecting temperature increases, and for measuring flow velocity.

7 Claims, 3 Drawing Figures

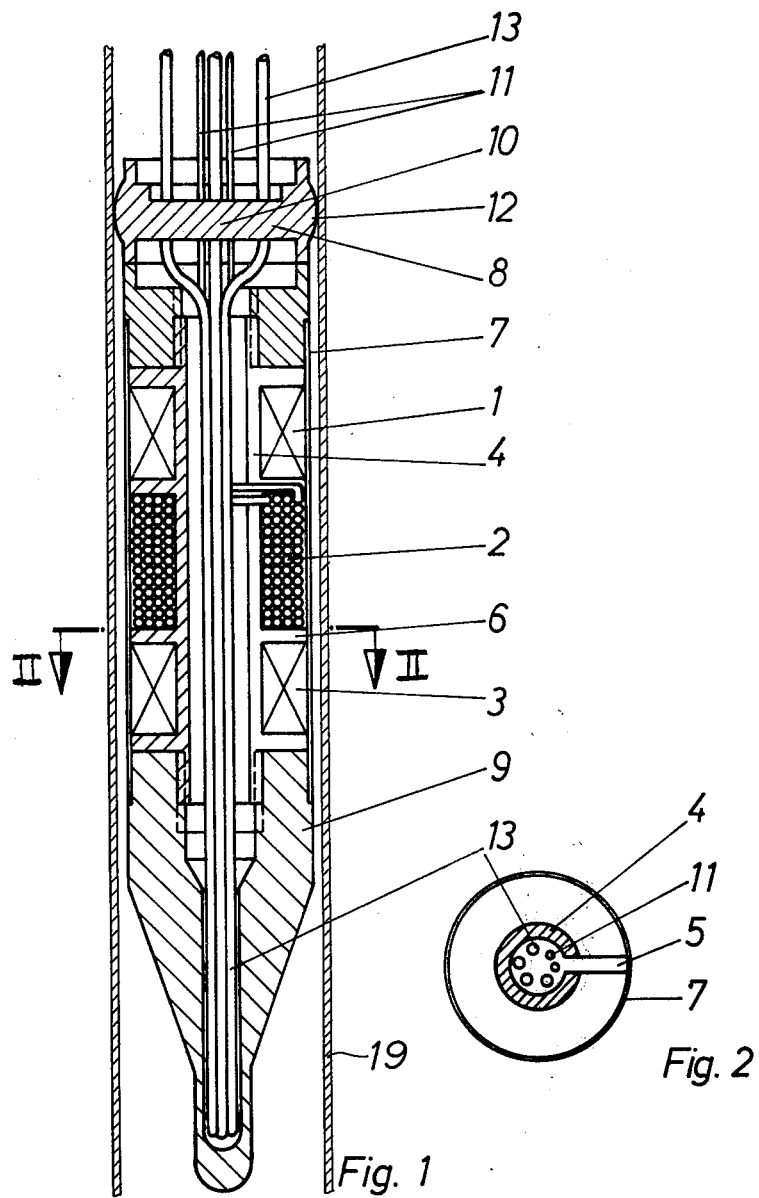

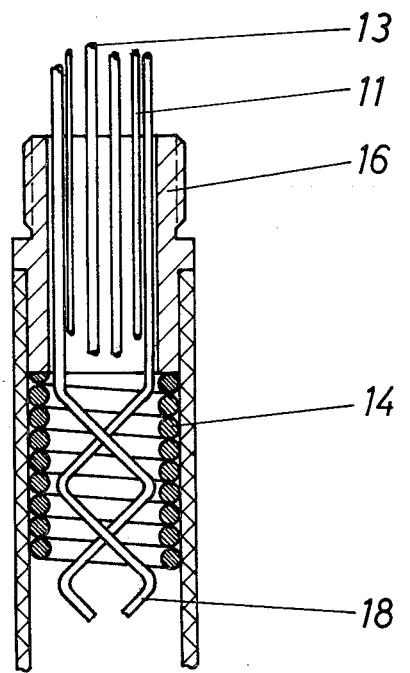
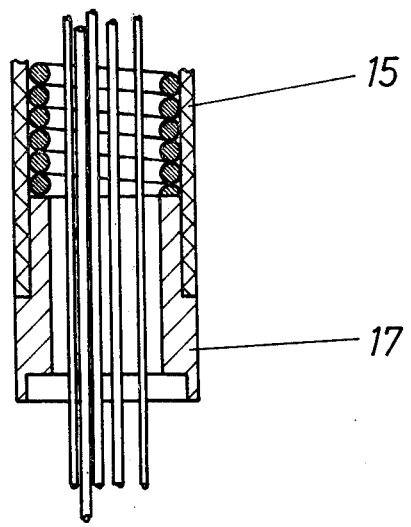
Fig. 3

METHOD AND DEVICE FOR REMOTELY MONITORING ELECTRICALLY CONDUCTIVE LIQUIDS

This is a continuation, of application Ser. No. 246,532, filed Apr. 24, 1972, now abandoned.

The invention relates to a method of remotely monitoring electrically conductive liquids, especially liquid sodium in nuclear power plants wherein, at the measuring location, at least three induction coils are provided. The invention relates as well to an interchangeable device, referred to hereinafter as a measuring head, for carrying out the aforementioned method.

A method of measuring the flow velocity of electrically conductive liquid by disposing parallel to the flow direction of the liquids at least three induction coils which are located on a common magnetic axis, the first and the third of these coils being excited by applying an alternating-current voltage thereto so that magnetic influence thereof upon the second coil mutually cancels when the flow is static or at a standstill, is known from U.S. Pat. No. 2,435,043. In this heretofore known method, the flow of the electrically conductive liquid past the coils causes a distortion of the magnetic fields of the first and the third coils, so that a voltage which is directly proportional to the velocity of the flow, is induced in the second coil. Applications of this known method to the measurement of the flow velocity of liquid sodium in nuclear power plants are known from BNES: London Conference on Fast Breeder Reactors, May 4 to 19, 1966, Chapter 18 and from ANL 7340, Argonne National Laboratory: "Summary Review of Flowmeters Suitable for Measuring Sodium Flow at Temperatures up to 1,200°F in the Fast Flux Test Facility".

From German PUblished Application 19 47 320 a device is known by means of which thermocouple elements are guided through tubes to measuring locations that are situated in the interior of a nuclear reactor.

An object of the invention of the instant application is to provide a method of remotely monitoring electrically conductive liquids, preferably liquid sodium, as well as a device for carrying out this method which, due to its construction and relatively small dimensions is suitable for use at locations that are poorly accessible, especially in the interior of a nuclear reactor and, more particularly for the installation thereof directly above the fuel elements.

An additional object of the invention is to provide such device which continuously measures the temperature and flow velocity as well as the bubble content, if desired, and with minimum delay, a suddenly occurring temperature increase of the liquid to be monitored. Monitoring of these factors or variables is required for proper and safe operation of the most varied installations, the measurement of the bubble content and sudden temperature increases in nuclear reactors being of particular significance since the formation of bubbles or a sudden temperature increase is almost always the result of operating troubles which can be caused, for example, by the rupturing of a fuel rod and the consequent escape of fission gas.

With the foregoing and other objects in view, we provide, in accordance with our invention, method of remotely monitoring electrically conductive liquid which includes placing at least three induction coils adjacent one another, at a location at which the electrically conductive liquid is to be monitored, exciting at least one of the coils, which serves as a primary coil, with alternating currents of different frequencies, and evaluating the voltages induced thereby in the adjacent coils, which serve as secondary coils, as a measure of at least one of the following factors: bubble content in the liquid, instantaneously detected temperature increases in the liquid, and flow velocity of the liquid.

In accordance with a further feature of the invention, the flow velocity of the liquid to be monitored is measured by exciting the primary coil with alternating current so as to generate secondary voltages in the secondary coils adjacent thereto, the secondary voltages being influenced by the flow past the secondary coils of the liquid to be monitored, correlating the influenced secondary voltages in differential connection through a conventional comparator circuit, with the temperature of the liquid measured at a different location therein by conventional circuit means, and indicating the measured values. The correlation of the secondary voltages with the temperature serves for compensating or equalizing differences in electrical conductivity at different temperatures which, in the case of the sodium, for example, may be rather considerable. An increase or decrease of the signal voltage obtained from the secondary coils when the temperature of the liquid is constant, therefor indicates higher or lower flow velocity, respectively. It has been found to be advantageous, in accordance with the invention, to use as excitation current an alternating current of relatively low frequency, for example 100 Hz because at higher frequencies a reduced depth of penetration into the liquid as well as higher attenuation and deviation from symmetry must be expected.

In accordance with a further feature of the invention, a modified method is provided which includes exciting the primary coil with an additional alternating current of relatively high frequency, for example 1000 Hz, measuring with a conventional pulse height analyzer the amplitude modulation of the voltages induced in the secondary coils and applying the measured amplitude modulation as a measure for the bubble content of the liquid being monitored. Bubbles in the liquid increase the ohmic resistance or resistivity of the liquid to a considerable extent, in fact, in proportion to the bubble content which, for the selected high frequency, results in heavy modulation of the amplitude of the secondary voltage. An analysis of the amplitude modulation, with respect to the height or magnitude thereof, is indicated or displayed by means of a conventional circuit, and provides a measure of the bubble content of the liquid. Because of the low depth of penetration of the field lines into the liquid at the relatively high frequency, it is desirable to guide the bubbles entrained by the liquid flow, by means of guide surfaces disposed in the flow, so that they flow past the coils a short distance therefrom.

In accordance with yet another feature of the invention, so as to detect instantaneously rapid temperature increases of the liquid to be monitored, the primary coil is excited with an alternating current, and the sum of the voltages induced in the secondary coils is applied as a measure of the temperature of the liquid to be monitored, wherein the variation in the electrical conductivity of the liquid, which occurs with an increase in temperature, is measured. This has the advantage that the measurement according to the invention, in contrast to a measurement with thermocouple elements, is effected virtually without any delay and that it covers, according to the depth of penetration of the field lines, a greater part of the liquid flow than merely that layer of lamina of the liquid flow which is in immediate contact with the measuring coil equipment. To this end, the high-frequency alternating voltages of the two secondary coils are added in a conventional circuit and converted into a signal proportional to the mean temperature of the liquid. In contrast to each individual secondary voltage, the sum of the two secondary voltages is, to a large extent, independent of the flow velocity of the liquid.

Further in accordance with the invention, there is provided a device for carrying out the foregoing method, which comprises an exchangeable measuring head that is secured to a manipulating tube in which measuring leads are received, the measuring head being slidingly disposed in a guide tube so as to be directed to a measuring location of the electrically conductive liquid.

According to other features of the invention, the measuring head contains at least three induction coils formed of metal-clad insulated wires that are wound on a common, hollow core of pure iron which is longitudinally slotted and is provided at the ends thereof and between the coils with circular ribs or cross-pieces which are interrupted by the slot. The coils are disposed coaxially behind one another, the middle one thereof being the primary or excitation coil, while the other two coils are the secondary coils. The use of metal-clad wire permits the device of the invention to be serviceable also at relatively high temperatures. It has been found that the proximity of the metal cladding of the wires to one another has no detrimental effect on the quality and intensity of the measuring signal in spite of the short-circuit currents produced thereby in the coils.

The coil core of pure iron which has a Curie point of 750°C, effects about a 30-fold increase in the signal voltage with respect to coils without cores that have been employed heretofore in corresponding devices, while the magnetic reluctance thereof, as compared for example to sodium, is so low that even any change produced in the permeability thereof due to radiation effects would have no effect on the accuracy of the measurement. The longitudinal slot formed in the core serves to damp or attenuate the eddy currents produced in the core and also facilitates the insertion of the wires therein. The core is further provided with circular ribs or cross-pieces of the same material as that of the core proper, which are located between the coils and at the outer ends thereof and cause the magnetic field lines of the coils to be deflected to a greater extent perpendicularly to the axis of the core and thereby to be more strongly distorted by the liquid flow, thereby intensifying the measured signal.

In accordance with an additional feature of the invention, it is proposed that the induction coils and their core be disposed in a closed protective tube. In addition to preventing mechanical damage to the coil, the protective tube also prevents any possibly nonuniform wetting as well as the deposition of impurities which might lead to faulty measurements and could also cause additional attenuation.

As a further feature of the invention when metalclad wires are used, the leads of the induction coils, which are received in the manipulating tube, form an integral unit with the wires of the respective induction coils. By dispensing with junctions of any kind, the operational reliability of the device is increased.

According to an added feature of the invention, the leads to the induction coils are tightly soldered in a passageway located at the end of the protective tube so that the measuring head forms a closed unit, and the leads are protected against damage by abrasion at the passageway.

In accordance with a further feature of the invention, at least one thermocouple element is provided in the measuring head. Consequently, the afore-mentioned temperature measurement required for determing the flow velocity is made at the same location of the installation or the liquid flow at which the velocity also is measured.

In accordance with a concomitant feature of the invention, the measuring head is connected with a flexible manipulating tube formed of a closely-wound wire spiral and at least one wire-netting tube braided thereover. This permits stressing of the tube both in tension as well as in compression in order to withdraw the device from the guide tube or to slide it into the same. The foregoing construction affords the capability of measuring these forces without damage to the tube, in that even considerable resistance, for example, due to jamming of the device in the guide tube can be overcome as each of both types of stress is absorbed by a separate member particularly suited therefor, both members being braced against one another. Further advantages of this construction is the possibility of guiding the measuring wires within the free interior space of the tube and the possibility of using the tube at high ambient temperatures. with this type of construction relatively small tube diameters of, for example, 12 mm, and small bending radii, of for example, 5m are furthermore attainable.

In accordance with yet another feature of the invention, the manipulating tube is provided in the interior thereof with a bifilar wound electric heater for melting any possibly solidified residue of the liquid, for example, solid sodium, which would otherwise interfere with handling or manipulation of the tube. It is also advantageous to make the measuring windings heatable, so that the measuring head can also be warmed.

Other features which are considered as characteristic for the invention are set forth in the appended claims.

Although the invention is illustrated and described herein as method and device for remotely monitoring electrically conductive liquids, it is nevertheless not intended to be limited to the details shown, since various modifications may be made therein without departing from the spirit of the invention and within the scope and range of equivalents of the claims.

The invention, however, together with additional objects and advantages thereof will be best understood from the following description when read in connection with the accompanying drawing, in which:

FIG. 1 is a diagrammatic longitudinal sectional view in axial plane of the measuring head of the invention in the instant application;

FIG. 2 is a cross-sectional view of FIG. 1 taken along the line II—II in the direction of the arrows;

FIG. 3 is a partly broken away longitudinal sectional view, in axial plane, of a flexible manipulating tube according to the invention.

Referring now to the drawings and first, particularly to FIG. 1 thereof, there is shown therein a primary coil 2 and secondary coils 1 and 3, formed entirely of metalclad insulated wire wound on a hollow cylindrical iron core 4 which is formed along the entire length thereof with a slot 5, and with cross-pieces or ribs 6 at the periphery thereof. The coils are disposed in a protective tube 7 which is provided with a base 8 and a tip 9. A passageway member or bushing 10, in which wires 11 are soldered, is secured to the base 8. The wires 11 lead to and from the coils 1 to 3, only one pair of the wires 11 being shown in FIG. 1 for the sake of clarity. The bushing 10 is provided with a peripheral bead 12 which guides the measuring head in the guide tube 19. Also soldered into the bushing 10 are wires 13 which are passed through the hollow iron core 4 up to the tip 9 and form a thermocouple element.

In FIG. 3 there is shown a manipulating tube according to the invention, which is formed of a closely-wound wire spiral 14 over which a wire netting tube 15 is braided. At each end of the tube 15 connector tubes 16 and 17 are, respectively, secured. In the interior of the manipulating tube of the invention there is provided a bifilar-wound electric heater 18.

We claim:

1. Device for carrying out a method of remotely monitoring electrically conductive liquid comprising an interchangeable measuring head, a manipulating tube wherein measuring leads are received, said measuring head being secured to said manipulating tube, a guide tube wherein said manipulating tube is slideably guidable to a given measuring location, at least three induction coils formed of metal-clad insulated wires wound on a common hollow core of pure iron that is provided with a longitudinal slot being received in said measuring head, and said core being formed with peripheral ribs at the ends thereof and between said coils, said peripheral ribs being interrupted by said slot.

2. Device according to claim 1, wherein said induction coils and said core thereof are disposed in a closed protective tube.

3. Device according to claim 1, wherein said measuring leads of said induction coils form an integral unit with the wires of the respective induction coils.

4. Device according to claim 3, wherein said induction coils and said core thereof are disposed in a closed protective tube, a passageway member secured to an end of said protective tube, said measuring leads of said induction coils being connected directly by soldering in said passageway member.

5. Device according to claim 1, including a thermocouple element disposed in said measuring head.

6. Device according to claim 1, wherein said manipulating tube is flexible and formed of a tightly wound wire spiral and at least one wire netting tube braided thereon, said measuring head being connected to said manipulating tube.

7. Device according to claim 6, including a bifilar wound electric heater disposed in said manipulating tube.

* * * * *